(12) United States Patent
Cynamon et al.

(10) Patent No.: US 11,992,195 B2
(45) Date of Patent: *May 28, 2024

(54) TRANSFEMORAL TRANSCAVAL LIVER ACCESS AND DEVICES

(71) Applicant: MONTEFIORE MEDICAL CENTER, Bronx, NY (US)

(72) Inventors: Jacob Cynamon, Suffern, NY (US); Deborah Eliana Cynamon, New York, NY (US); Yosef Golowa, Spring Valley, NY (US)

(73) Assignee: MONTEFIORE MEDICAL CENTER, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,092

(22) Filed: Oct. 7, 2022

(65) Prior Publication Data

US 2023/0181175 A1 Jun. 15, 2023

Related U.S. Application Data

(63) Continuation of application No. 16/659,169, filed on Oct. 21, 2019, now Pat. No. 11,504,100, which is a continuation of application No. 15/533,384, filed as application No. PCT/US2016/013576 on Jan. 15, 2016, now Pat. No. 10,448,931.

(60) Provisional application No. 62/103,821, filed on Jan. 15, 2015.

(51) Int. Cl.
*A61B 10/02* (2006.01)
*A61B 17/00* (2006.01)
*A61B 17/34* (2006.01)

(52) U.S. Cl.
CPC ...... *A61B 10/0233* (2013.01); *A61B 17/3415* (2013.01); *A61B 2017/00946* (2013.01)

(58) Field of Classification Search
CPC ............ A61B 10/0233; A61B 17/3415; A61B 2017/00946
See application file for complete search history.

(56) References Cited

U.S. PATENT DOCUMENTS

| | | | |
|---|---|---|---|
| 4,327,722 A * | 5/1982 | Groshong | A61M 25/06 604/510 |
| 5,273,051 A * | 12/1993 | Wilk | A61B 10/04 600/564 |
| 5,639,276 A | 6/1997 | Weinstock | |
| 5,807,330 A | 9/1998 | Teitelbaum | |
| 5,876,385 A * | 3/1999 | Ikari | A61M 25/0041 604/523 |
| 6,419,641 B1 | 7/2002 | Mark et al. | |
| 7,078,694 B2 | 7/2006 | Polonsky et al. | |
| 7,402,151 B2 | 7/2008 | Rosenman | |
| 7,841,990 B2 | 11/2010 | Mark et al. | |
| 10,448,931 B2 | 10/2019 | Cynamom | |

(Continued)

OTHER PUBLICATIONS

Ki Tae Suk, "Hepatic venous pressure gradient: clinical use in chronic liver disease", 2014, Clinical and Molecular Hepatology. (Year: 2014).*

(Continued)

*Primary Examiner* — Eric F Winakur
*Assistant Examiner* — Abid A Mustansir
(74) *Attorney, Agent, or Firm* — Perkins Coie LLP

(57) ABSTRACT

Shaped liver biopsy sheaths and methods for transfemoral transcaval liver access are disclosed.

20 Claims, 6 Drawing Sheets

(56) References Cited

U.S. PATENT DOCUMENTS

| | | | |
|---|---|---|---|
| 11,504,100 | B2 | 11/2022 | Cynamom |
| 2003/0014008 | A1 | 1/2003 | Jacques |
| 2003/0125725 | A1 | 7/2003 | Woodward et al. |
| 2006/0135961 | A1* | 6/2006 | Rosenman ......... A61B 17/0057 604/95.04 |
| 2007/0021739 | A1 | 1/2007 | Weber |
| 2007/0213634 | A1* | 9/2007 | Teague ............... A61B 10/0266 600/564 |
| 2007/0250160 | A1 | 10/2007 | Rafiee |
| 2007/0260196 | A1 | 11/2007 | Belsley |
| 2009/0156995 | A1 | 6/2009 | Martin et al. |
| 2009/0326373 | A1* | 12/2009 | Boese ....................... G06T 7/38 600/440 |
| 2013/0018408 | A1* | 1/2013 | Farley ................ A61B 17/0206 606/198 |
| 2014/0180164 | A1 | 6/2014 | McGhie |

OTHER PUBLICATIONS

Bruzzi JF et al., "Transjugular liver biopsy: assessment of safety and efficacy of the Quick-Core biopsy needle." Abdom Imaging 2002; 27:711-715.

Cynamon J. et al., "Transfemoral Transcaval Core-Needle Liver Biopsy: An Alternative to Transjugular Liver Biopsy." J Vasc. Interv. Radiol., Epub Dec. 23, 2015, 6 pages.

Dohan A. et al., "Major complications due to transjugular liver biopsy: incidence, management and outcome." Diagn Interv Imaging 2015; 96:571-577.

Gamble P. et al., "Transjugular liver biopsy: a review of 461 biopsies." Radiology 1985; 157:589-593.

International Search Report and Written Opinion dated Mar. 16, 2016 in International Patent Application No. PCT/US16/13576, 9 pages.

Mammen, T. et al., "Transjugular liver biopsy: a retrospective analysis of 601 cases." J Vasc Inten1 Radiol 2008; 19: 351-358.

Moses, V. et al., "Trans-caval trans-jugular liver biopsy—a technical modification of trans-jugular liver biopsy." Br J Radial 2014; 87:20140327.

Rosch, J. et al., "Transjugular approach to liver biopsy and transhepatic cholangiography." N Engl J Med 1973; 289: 227-231.

Sacks, D. et al., "Society of Interventional Radiology clinical practice guidelines." J Vasc Interv Radiol 2003;14:SI99-S202.

Smith, TP et al., "Transjugular biopsy of the liver in pediatric and adult patients using an 18-gauge automated core biopsy needle: a retrospective review of 410 consecutive procedures." AJR Am J Roentgenol 2003;180:167-172.

\* cited by examiner

TRANSFEMORAL TRANSCAVAL LIVER ACCESS AND DEVICES

CROSS-REFERENCE TO RELATED APPLICATION

This application is a continuation of U.S. application Ser. No. 16/659,169, filed Oct. 21, 2019, now U.S. Pat. No. 11,504,100, issued on Nov. 22, 2022, which is a continuation of U.S. application Ser. No. 15/533,384, filed Jun. 6, 2017, now U.S. Pat. No. 10,448,931, issued on Oct. 22, 2019, which is a national phase of International Application No. PCT/US2016/013576, filed Jan. 15, 2016, which claims the benefit of U.S. Provisional Patent Application No. 62/103,821, filed on Jan. 15, 2015, the content of which is herein incorporated by reference into the subject application.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Liver biopsy is the gold standard for the evaluation of acute and chronic liver disease. Percutaneous liver biopsy (PLB) remains the preferred approach in most situations; however, transjugular liver biopsy (TJLB) (1) can be performed where there are contraindications to a percutaneous approach, such as coagulopathy, thrombocytopenia or ascites where PLB may be prone to bleeding (2-4). TJLB is considered safer in these situations since any bleed will most likely be intravascular.

However, TJLBs can be difficult, and there are potential complications. TJLB requires hepatic vein cannulation through which the biopsy specimen is obtained. Difficulties include negotiating a stiffened cannula into acutely angled hepatic veins; maintaining a stiff cannula in the hepatic vein during movement caused by the patient's respiration while avoiding injury of the hepatic vein/liver junction, and the need for two operators—one to hold the cannula and one to remove the biopsy specimen from the needle.

Biopsies performed directly through the inferior vena cava (IVC) from a jugular approach have also been described in instances when a hepatic vein could not be cannulated (5). Difficulties with this approach can include difficult jugular access and the need to traverse and exit the right atrium (RA) into the IVC.

The present invention provides procedures and devices for a transfemoral transcaval (TFTC) approach for liver biopsies that is expected to be safer, easier and more reliable than a transjugular approach.

SUMMARY OF THE INVENTION

The present invention provides methods of obtaining a tissue sample from the liver of a patient, the methods comprising inserting a hollow sheath, such as a stiffened sheath with an angled tip, through a femoral vein into a portion of the inferior vena cava (IVC) adjacent to the liver, wherein the sheath's tip is in the intrahepatic IVC and wherein the sheath has a shape that brings the tip of the sheath adjacent to the wall of the IVC at an angle that is optimal to allow penetration of the wall of the IVC by a biopsy needle, and inserting a biopsy needle through the sheath and through the wall of the IVC into the liver to obtain a tissue sample from the liver.

The invention also provides kits for obtaining a tissue sample from the liver of a patient, the kits comprising an outer flexible vascular sheath having a length that extends from a femoral vein to the intrahepatic portion of the inferior vena cava (IVC) of the patient; a hollow sheath, such as a stiffened angled sheath, capable of passing through the outer flexible sheath, wherein the sheath is preshaped with one or more bends and/or is capable of being shaped in vivo to provide an angle between the tip of the sheath and the longitudinal axis of the sheath between >30 degrees to 90 degrees, and wherein the hollow sheath is longer than the outer flexible vascular sheath; and a flexible biopsy needle capable of passing through the hollow sheath to penetrate the wall of the IVC and pass into the liver to obtain a tissue sample from the liver, wherein the flexible biopsy needle is longer than the hollow sheath.

DETAILED DESCRIPTION OF THE INVENTION

Figure 1:
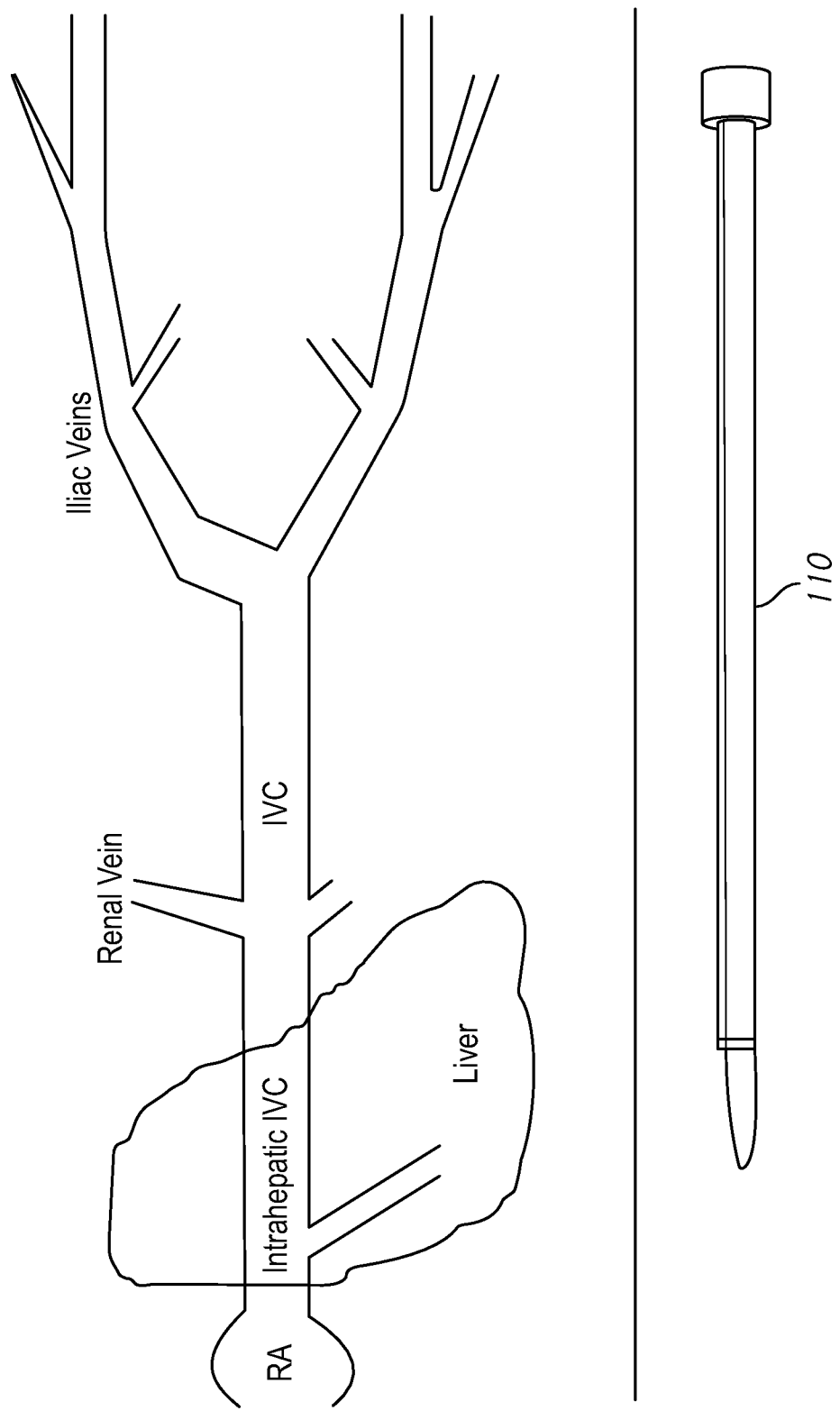
FIG. 1. Schematic of venous anatomy and an example of an outer flexible vascular sheath 110. The femoral veins are to the right of the venous diagram. IVC—inferior vena cava, RA—right atrium. Drawing not to scale.

The present invention provides a method of obtaining a tissue sample from a liver of a patient, via a transfemoral transcaval route, the method comprising:

inserting a hollow sheath through a femoral vein into a portion of the inferior vena cava (IVC) adjacent to the liver, wherein the sheath's tip is in the intrahepatic IVC and wherein the sheath has a shape that brings the tip of the sheath adjacent to the wall of the IVC at an angle that is optimal to allow penetration of the wall of the IVC by a biopsy needle, and inserting a biopsy needle through the sheath and through the wall of the IVC into the liver to obtain a tissue sample from the liver.

The sheath can be preshaped with one or more bends before the sheath is inserted into the patient. Alternatively, or in addition, the sheath can be shaped in vivo after the sheath is inserted into the IVC. The sheath may have, for example, one bend 222 or 322 (FIG. 2 or 3) near the tip and a secondary bend 223 or 323 (FIG. 2 or 3) in the longitudinal axis of the sheath farther from the tip.

The sheath can be inserted through an outer vascular sheath that has been inserted through the femoral vein into the IVC.

The sheath and/or outer vascular sheath can be inserted in the IVC with the aid of a guidewire.

The sheath has a main longitudinal body that can contain one or more bends (e.g., bends 222, 223, 322, and/or 323 illustrated in FIG. 2 or 3) to angle the tip of the sheath so that it is optimal to allow penetration of the wall of the IVC by a biopsy needle. The angle of the tip is indicated in reference to the longitudinal axis of the main body of the sheath (i.e., the main part of the sheath that is not bent). The angle between the tip of the sheath and the longitudinal axis of the sheath is preferably between >30 degrees to 90 degrees or 35-90 degrees or 40-90 degrees. In one embodiment, the angle between the tip of the sheath and the longitudinal axis of the sheath is between 40-80 degrees. In one embodiment, the angle between the tip of the sheath and the longitudinal axis of the sheath is between 50-70 degrees.

Preferred sheaths include those that are malleable to allow the introduction of secondary bends along the main body of the sheath.

The invention also provides a kit for obtaining a tissue sample from the liver of a patient, the kit comprising:
an outer flexible vascular sheath having a length that extends from a femoral vein to an intrahepatic portion of the inferior vena cava (IVC) of the patient;
a hollow sheath capable of passing through the outer flexible sheath, wherein the sheath is preshaped with one or more bends and/or is capable of being shaped in vivo to provide an angle between the tip of the sheath and the longitudinal axis of the sheath between >30 degrees to 90 degrees, and wherein the hollow sheath is longer than the outer flexible vascular sheath; and
a flexible biopsy needle capable of passing through the hollow sheath to penetrate the wall of the IVC and pass into the liver to obtain a tissue sample from the liver, wherein the flexible biopsy needle is longer than the hollow sheath.

The kit can also include a guidewire to add insertion and placement of the outer flexible vascular sheath and/or hollow sheath in the IVC; and/or a dilator.

In different embodiments, the angle between the tip of the sheath and the longitudinal axis of the sheath is between 35-90 degrees, 40-90 degrees, 40-80 degrees or 50-70 degrees.

The kits disclosed herein can be used for obtaining a tissue sample from the liver of a patient.

The components of the present invention can be made from standard materials used in vascular surgery and biopsies. For example, the outer vascular sheath can be a 10-F sheath of 38.5 cm, such as provided, for example, by Cook, Inc., Bloomington, Indiana. The guidewire, if used, can be, for example, a 0.035-inch guide wire.

Figure 2:
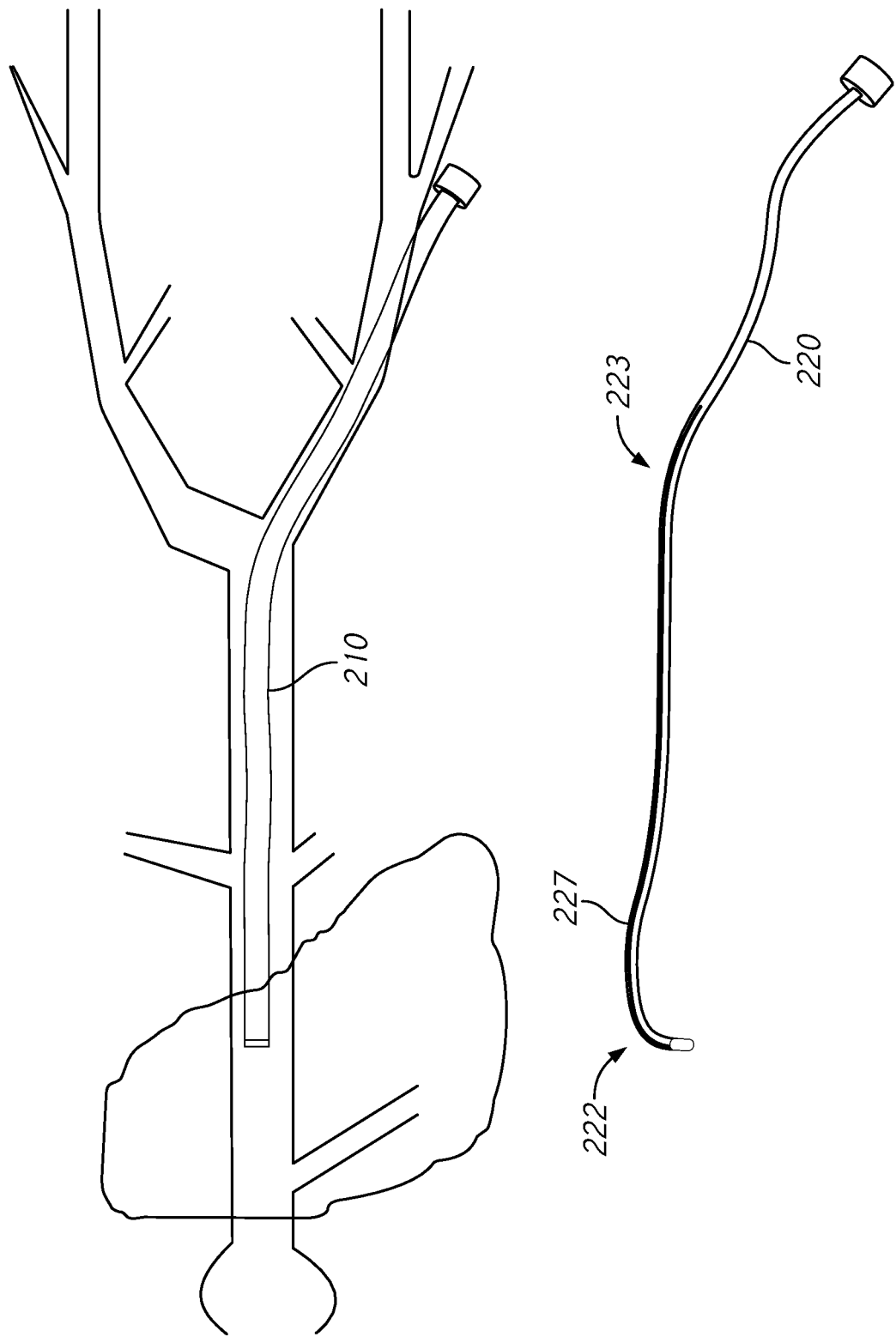
FIG. 2. Illustration of an example of a schematic of an outer flexible vascular sheath 210 inserted through the femoral vein into the IVC to the level of the liver and of a preshaped rigid hollow sheath 220 that can be inserted through the outer flexible vascular sheath. Drawing not to scale.
Figure 3:
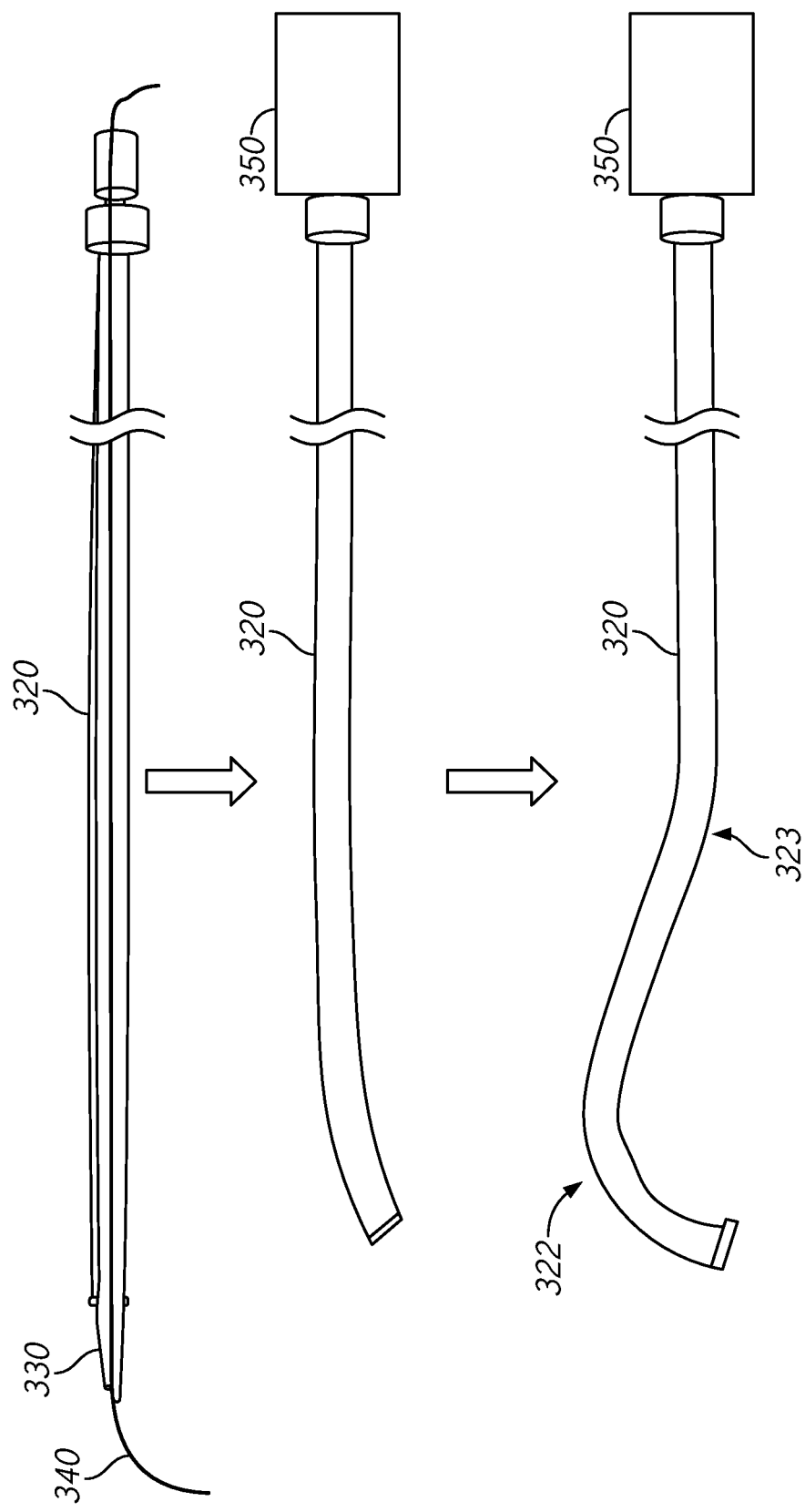
FIG. 3. Illustration of an example of a shapeable semirigid hollow sheath 320 (and dilator 330) that can be inserted over a guidewire 340 into the IVC. The assembly is shown in the upper view of the figure. The guidewire 340 and dilator 330 can be removed from the hollow sheath 320 (middle view) and the hollow sheath can be shaped in vivo into an optimal shape for a transcaval liver biopsy (lower view). Drawing not to scale.

The preshaped sheath can be, for example, a 7-F stiffened cannula. Such cannulas can be provided by Argon Medical Devices, Inc., Athens, Texas. The preshaped sheath can have a precurved protective metallic insert or stiffener 227 (FIG. 2). The preshaped sheath needs to be preshaped with one or more bends to provide an angle of incidence of the tip of the sheath with respect to the wall of the IVC that is optimal to allow penetration of the wall of the IVC by a biopsy needle. Existing preshaped devices on the market are not meant to be reshaped, due to concerns about damaging the device. Accordingly, no preshaped device currently exists on the market that provides a tip angle suitable for a transfermoral transcaval liver biopsy as disclosed herein. Alternatively, or in addition to, a preshaped sheath, the sheath can be shaped in vivo using, for example, a mechanical handle 330 (FIG. 3) at the external end of the sheath. Catheters with ends that can be adjusted to change shape have been described, for example, in U.S. Pat. No. 7,402,151 B2 (BioCardia, Inc., South San Francisco, CA), the contents of which are herein incorporated by reference. Whereas preshaped sheaths will typically be advanced into the IVC through a pre-positioned outer vascular sheath, flexible sheaths that can be shaped in vivo may not need to be advanced into the IVC through a pre-positioned outer vascular sheath due to the flexibility of the sheath. The length of the sheath needs to be sufficient to reach from the femoral vein to the intrahepatic IVC of the patient and can be, for example, about 70 cm long.

The flexible biopsy needle can be, for example, a 19-gauge biopsy needle with a 20-mm throw, such as provided, for example, by Argon Medical Devices, Inc., Athens, Texas Biopsy devices are described, for example, in U.S. Pat. Nos. 6,419,641 B1, 7,078,694 B2 and 7,841,990 B2 (Promex Technologies, LLC, Franklin, IN), the contents of which are incorporated herein. The biopsy needle needs to be longer than the sheath so that the needle can penetrate the wall of the IVC and enter the liver.

Placement of the sheaths and biopsy needle can be monitored by real-time imaging of the patient.

Advantages of the transfemoral, transcaval approach disclosed herein include:
no need for jugular access and its inherent complications,
no need to cross the right atrium and its inherent complications (arrhythmias, tamponade, etc.),
no need to advance a rigid cannula into a hepatic vein,
multiple biopsies can be obtained without the need to hold the cannula in place,
a single operator can perform the entire procedure—perform biopsy and remove the specimen from needle, and
pressures (RA, IVC, HV and/or Wedge PV) can be easily obtained from the femoral route.

This invention will be better understood from the Experimental Details, which follow. However, one skilled in the art will readily appreciate that the specifics discussed are merely illustrative of the invention as described more fully in the claims that follow thereafter.

EXPERIMENTAL DETAILS

Example I—Overview of Obtaining Hepatic Tissue Through the Inferior Vena Cava Through a Femoral Venous Approach The invention involves inserting a sheath through a femoral vein into the inferior vena cava (IVC) to the level of the liver of a patient. The advancement and positioning the sheath can be monitored by real-time imaging of the patient.

Examples of sheaths that can be used are illustrated in FIGS. 1-4. A biopsy needle is then inserted through the sheath to penetrate the wall of the IVC and obtain a tissue sample from the liver. The sheath is positioned so that the angle of incidence of the tip of the sheath with respect to the wall of the IVC is optimal to allow penetration of the wall of the IVC by the biopsy needle.

Figure 4:
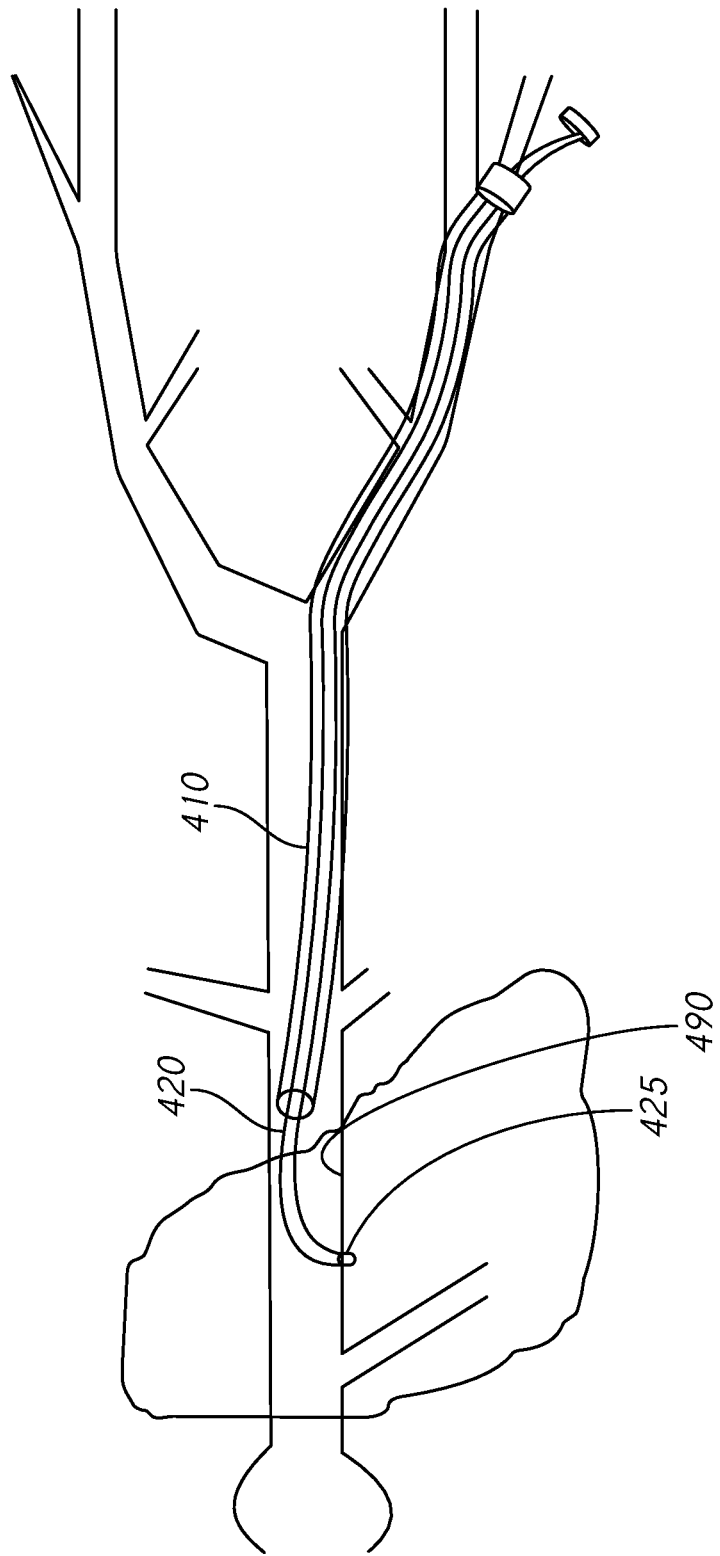
FIG. 4. Illustration of an example of an inner hollow sheath 420 that has been advanced through an outer flexible vascular sheath 410 so that a tip 425 of the inner hollow sheath 420 is positioned at a desired angle relative to a wall 490 of the IVC. The inner hollow sheath 420 can be a preshaped rigid hollow sheath or a shapeable semirigid hollow sheath having a tip 425 that can be shaped in vivo. A flexible biopsy needle 580 (illustrated in FIG. 5) can be advanced through the inner hollow sheath 420 to penetrate the wall 490 of the IVC and obtain a tissue sample from the liver. Drawing not to scale.
Figure 5:
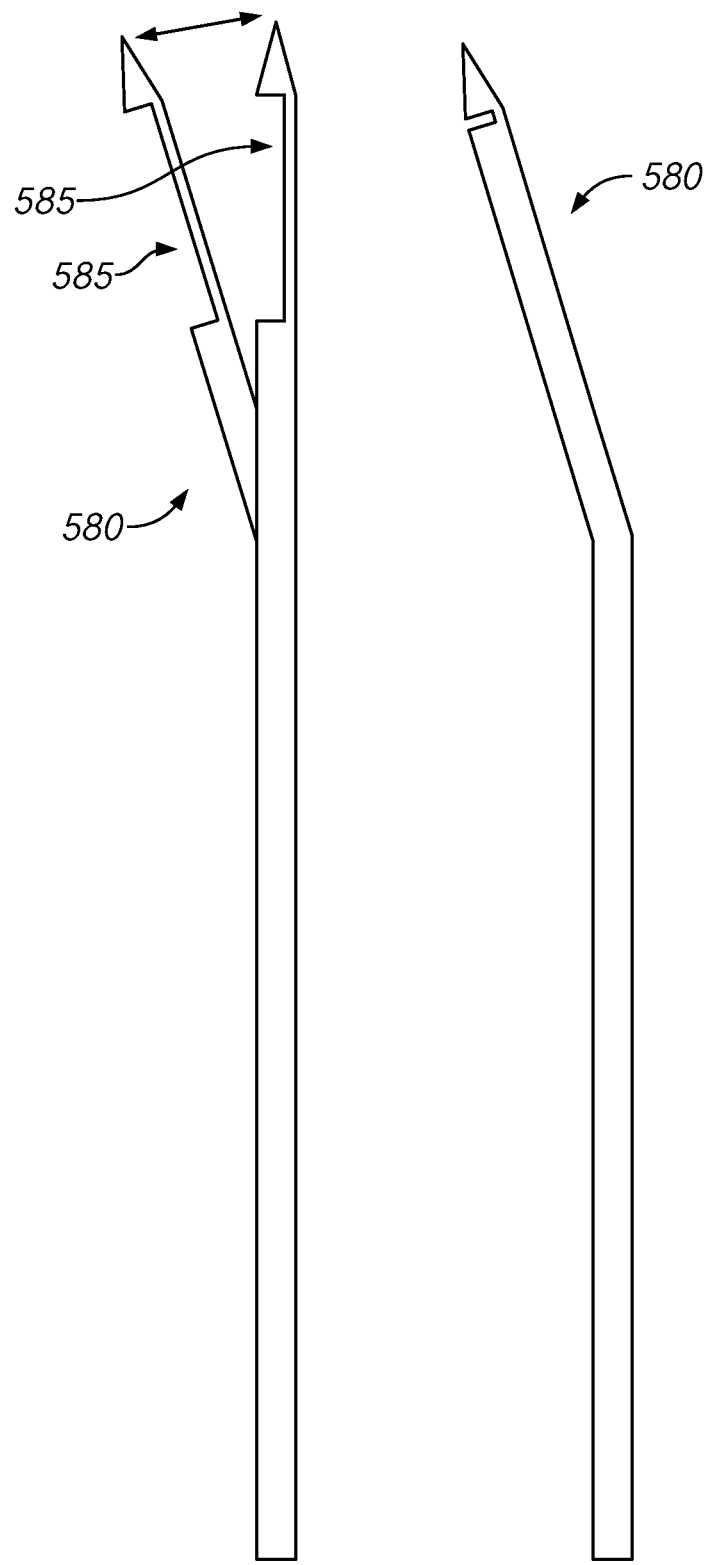
FIG. 5. Examples of a flexible biopsy needle 580. Left—example of a flexible biopsy needle 580 demonstrating range of flexibility. A window 585 for collecting the biopsy sample is open. Right—example of a flexible biopsy needle 580 with the core biopsy window closed.

FIGS. 1 and 2 illustrate an example of a vascular sheath that is inserted through a femoral vein to the intrahepatic IVC. The sheath can be positioned in the vasculature using a guidewire. FIG. 4 illustrates an example of an inner sheath positioned though an outer vascular sheath so that the tip of the inner sheath is at a desired angle with respect to the wall of the IVC. The inner sheath can be preshaped prior to being inserted through the outer vascular sheath (e.g., FIG. 2, Item 2—preshaped rigid sheath). Alternatively, the tip of the sheath can be shaped after the sheath is placed into the intrahepatic IVC (e.g., FIG. 3), in which case an outer vascular sheath may not be required.

Example II—Obtaining Hepatic Tissue Through the Inferior Vena Cava Through a Femoral Venous Approach. This Example is Summarized from Cynamon, J., et al. (9). See also (10)

Materials and Methods

The institutional review board approved this retrospective study. Sixty-six cases of transfemoral transcaval (TFTC) liver biopsies (65.2% male; mean age, 53.2±15.0 years) were reviewed. One patient underwent three TFTC biopsies; each was counted individually.

Abnormal coagulation parameters were defined by institutional laboratory thresholds. All patients with an international normalized ratio≥1.8 or platelet count<50,000/µL were transfused with fresh frozen plasma or platelets, respectively, immediately before the procedure, during the procedure, or both. Intravenous fentanyl and midazolam were administered for sedation at the operator's discretion. Patient oxygen saturation, hemodynamics, and electrocardiographic parameters were monitored during the case. After biopsy, patients were observed and vital signs were monitored for at least 4 hours. Procedure-related complications were classified according to Society of Interventional Radiology (SIR) guidelines (6).

Figure 6:
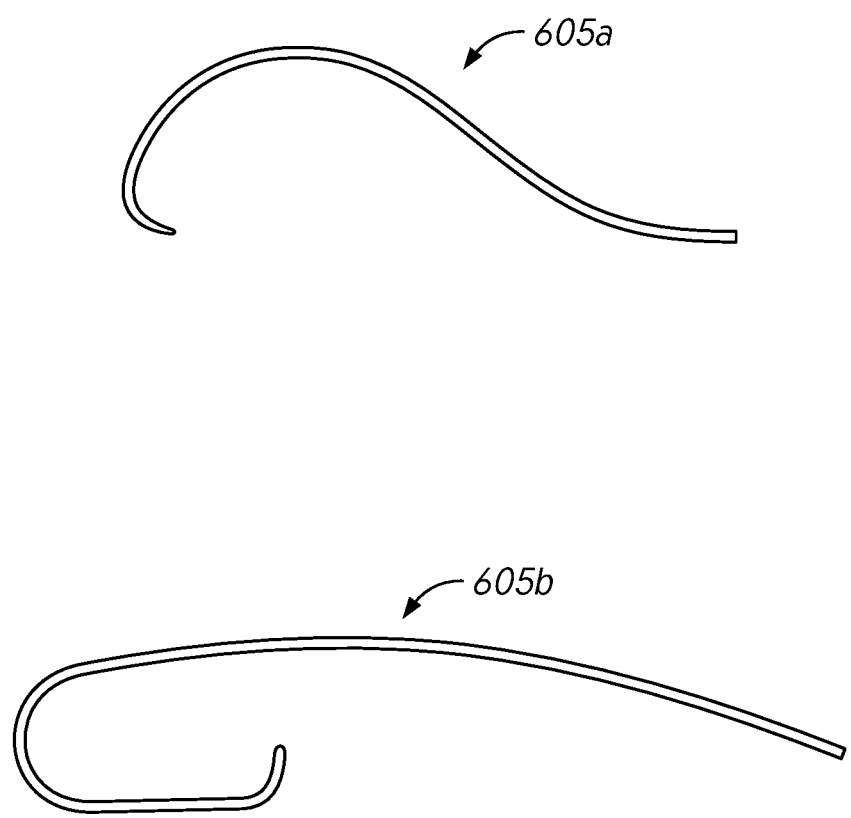
FIG. 6. Illustration of example selective catheters 605a and 605b.

Right common femoral venous access was obtained using the Seldinger technique, and a 38.5-cm-long 10-F sheath (Flexor® Check-Flo® II; Cook, Inc., Bloomington, Indiana) was placed over a 0.035-inch guidewire into the inferior vena cava (IVC). The sheath dilator was then exchanged for a selective catheter such as a 5-F Cobra selective catheter 605a (Cook, Inc.) or a 6-F Judkins Left 4 selective catheter 605b (Cook, Inc.) illustrated in FIG. 6. The catheter was used to select a hepatic vein to measure hepatic venous pressure.

Next, the catheter was exchanged for a physician-modified (with slight increase in curvature) precurved 7-F stiffened cannula (Argon Medical Devices, Plano, Texas), which was advanced through the long sheath over the guide wire and positioned in the intrahepatic IVC. This cannula was directed toward the lateral caval wall within the intrahepatic portion of the IVC at a level deemed favorable based on imaging.

Next, a 19-gauge biopsy needle (Flexcore, Argon Medical Devices) with a 20-mm throw was advanced through the caval wall, and the biopsy needle was fired under fluoroscopic observation. The stiffened cannula was repositioned slightly more inferiorly, and a second biopsy specimen was obtained in a similar fashion. Tissue samples were examined by the operator, and if deemed inadequate, additional samples were obtained. A venogram was then obtained through the sheath to document absence of caval injury before removal.

Results and Discussion

Hepatic tissue samples were obtained in 64 out of 66 cases (97%). Sufficient tissue for histopathologic diagnosis was obtained in 63 cases (95.5%). Complications after biopsy occurred in only two patients (3%), which were successfully treated. One of the two was a decrease in hemoglobin and the second was a self-limiting fever. No bleeding complications were observed.

One advantage of the TFTC approach is that the procedure does not require traversing the right atrium, which occasionally may be difficult or lead to arrhythmias (2,7,8). This method also avoids the need to advance and maintain a stiff cannula in a hepatic vein, and obviates negotiating problematic hepatic venous anatomy. Performing the biopsy directly from the IVC also does not necessitate a lateral view to distinguish between the right and middle hepatic veins when the correct catheter position is in question (2,7), as is required for the TJLB procedure. Additionally, the biopsy needle is deployed within the liver directly through the intrahepatic IVC away from central vessels so that arterial and capsular injuries may be avoided. Finally, positioning and maintaining the physician-modified cannula against the lateral caval wall during and between biopsies does not require more than one operator. The overall technical and histopathologic success rates in this study, which were 97.0% and 95.5%, respectively, are similar compared to prior large case series of TJLBs (2,3,7,8). TFTC liver biopsies are safe and have advantages over TJLB.

REFERENCES

1. Misch J, Lakin P C, Antonovic R, Dotter C T. Transjugular approach to liver biopsy and transhepatic cholangiography. N Engl J Med 1973; 289:227-231.
2. Mammen T, Keshava,S N, EapenCE, et al. Transjugular liver biopsy: a retrospective analysis of 601 cases. J Vasc Intery Radiol 2008; 19:351-358.
3. SmithTP, Presson T L, Heneghan M A, Ryan J M. Transjugular biopsy of the liver in pediatric and adult patients using an18-gauge automated core biopsy needle: a retrospective review of 410 consecutive procedures. AJR Am J Roentgenol 2003; 180:167-172.
4. Bruzzi J F, O'Connell M J, Thakore H, O'Keane C, Crowe J, Murray J G. Transjugular liver biopsy: assessment of safety and efficacy of the Quick-Core biopsy needle. Abdom Imaging 2002; 27:711-715.
5. Moses V, Keshava S N, Mammen S, Ahmed M, Eapen C E, Ramakrishna B. Trans-caval trans-jugular liver biopsy—a technical modification of trans-jugular liver biopsy. Br J Radiol 2014; 87:20140327.
6. Sacks D, McClenny T E, Cardella J F, Lewis C A. Society of Interventional Radiology clinical practice guidelines. J Vasc Intery Radiol 2003; 14:S199-S202.
7. Gamble P, Colapinto R F, Stronell R D, Colman J C, Blendis L.Transjugular liver biopsy: a review of 461 biopsies. Radiology 1985; 157:589-593.
8. Dohan A, Guerrache Y, Dautry R, et al. Major complications due to transjugular liver biopsy: incidence, management and outcome.Diagn Intery Imaging 2015; 96:571-577.
9. Cynamon J, Shabrang C, Golowa Y, Daftari A, Herman O, Jagust M. Transfemoral Transcaval Core-Needle Liver Biopsy: An Alternative to Transjugular Liver Biopsy. J Vasc. Interv. Radiol., Epub Dec. 23, 2015, 6 pages.

10. Daftari A, Golowa Y, Jagust M, Herman O, Cynamon J. Feasibility of transcaval needle core biopsies from a femoral vein approach. J Vasc. Interv. Radiol., February 2015:26(2): S84.

What is claimed is:

1. A method of obtaining a tissue sample from a liver of a patient, the method comprising:
   inserting a hollow sheath through a femoral vein into a portion of the inferior vena cava (IVC) adjacent to the liver such that the hollow sheath has a tip portion positioned in the intrahepatic IVC with an opening directed toward a wall of the IVC; and
   inserting the flexible biopsy needle through the hollow sheath, through the opening, through the wall of the IVC, and into the liver to obtain a tissue sample from the liver.

2. The method of claim 1, wherein:
   the method further comprises inserting an outer vascular sheath through the femoral vein into the IVC; and
   after inserting the outer vascular sheath, inserting the hollow sheath through the femoral vein into the portion of the IVC adjacent via the outer vascular sheath.

3. The method of claim 1, wherein the hollow sheath, at least when inserting the flexible biopsy needle through the hollow sheath, includes one or more bends at or proximate the tip portion such that an angle between the tip portion and a longitudinal axis of the hollow sheath directs the opening toward the wall of the IVC.

4. The method of claim 3, wherein:
   the one or more bends includes a first bend at a first location and a second bend at a second location farther from the tip portion than the first location; and
   the first bend includes a radius of curvature that is lesser than a radius of curvature of the second bend.

5. The method of claim 3, wherein the angle between the tip portion and the longitudinal axis of the hollow sheath is between 40 degrees and 80 degrees.

6. The method of claim 3 wherein the angle between the tip portion and the longitudinal axis of the hollow sheath is between 50 degrees and 70 degrees.

7. The method of claim 3, wherein inserting the hollow sheath includes shaping the hollow sheath in vivo such that the hollow sheath includes the one or more bends.

8. The method of claim 7, wherein shaping the hollow sheath in vivo includes introducing the one or more bends into the hollow sheath using a mechanical handle located at an end of the hollow sheath that is positioned external to the patient.

9. The method of claim 3, wherein the hollow sheath is preshaped to include the one or more bends prior to inserting the hollow sheath through the femoral vein into the portion of the IVC adjacent to the liver.

10. The method of claim 9, wherein the one or more bends correspond to a metallic insert or stiffener of the hollow sheath that is precurved prior to inserting the hollow sheath through the femoral vein into the portion of the IVC adjacent to the liver.

11. The method of claim 1, further comprising inserting a guidewire through the femoral vein into the IVC.

12. The method of claim 11, wherein inserting the hollow sheath includes inserting, using the guidewire, the hollow sheath and a dilator positioned within the hollow sheath through the femoral vein and into the IVC.

13. The method of claim 12, further comprising:
   removing the dilator from within the hollow sheath;
   inserting, through the hollow sheath, a selective catheter through the femoral vein; and
   selecting a hepatic vein to measure hepatic venous pressure.

14. The method of claim 1, further comprising obtaining the tissue sample from the liver using the flexible biopsy needle.

15. The method of claim 14, wherein obtaining the tissue sample includes firing the flexible biopsy needle, wherein firing the flexible biopsy needle includes closing a biopsy sampling window of the flexible biopsy needle.

16. The method of claim 14, wherein inserting the flexible biopsy needle and obtaining the tissue sample include inserting the flexible biopsy needle and obtaining the tissue sample using real-time imaging.

17. The method of claim 14, wherein:
   the tissue sample is a first tissue sample obtained at a first location in the liver; and
   the method further comprises
      after obtaining the first tissue sample, repositioning the flexible biopsy needle to a second location in the liver, and
      obtaining, using the flexible biopsy needle, a second tissue sample from the second location in the liver.

18. The method of claim 1, wherein inserting the hollow sheath includes inserting the hollow sheath through the femoral vein into the portion of the IVC without use of an outer vascular sheath in which the hollow sheath is positionable.

19. The method of claim 1, wherein inserting the hollow sheath includes inserting the hollow sheath through the femoral vein into the portion of the IVC using real-time imaging.

20. The method of claim 1, wherein inserting the flexible biopsy needle into the liver includes inserting the flexible biopsy needle directly into the liver via the IVC.

* * * * *